United States Patent
Konoike et al.

Patent Number: 5,463,107
Date of Patent: Oct. 31, 1995

[54] TRITERPENE DERIVATIVES AND ENDOTHELIN-RECEPTOR ANTAGONISTS CONTAINING THE SAME

[75] Inventors: Toshiro Konoike, Suita; Yoshitaka Araki, Higashiosaka; Tetsuyoshi Hayashi, Otsu; Kensuke Sakurai, Nara; Takehiko Tozyo, Kobe, all of Japan

[73] Assignee: Shionogi & Co., Ltd., Japan

[21] Appl. No.: 258,392

[22] Filed: Jun. 10, 1994

[30] Foreign Application Priority Data

Jun. 11, 1993 [JP] Japan .................... 5-140416

[51] Int. Cl.$^6$ ................. C07C 211/43
[52] U.S. Cl. ................... 560/43; 562/441
[58] Field of Search ............. 560/43; 562/441

[56] References Cited

FOREIGN PATENT DOCUMENTS 0526642 2/1993 European Pat. Off. .
0526642A1 2/1993 European Pat. Off. .

Primary Examiner—José G. Dees
Assistant Examiner—Joseph M. Conrad, III
Attorney, Agent, or Firm—Wenderoth, Lind & Ponack

[57] ABSTRACT

Triterpene derivatives of the formula (I):

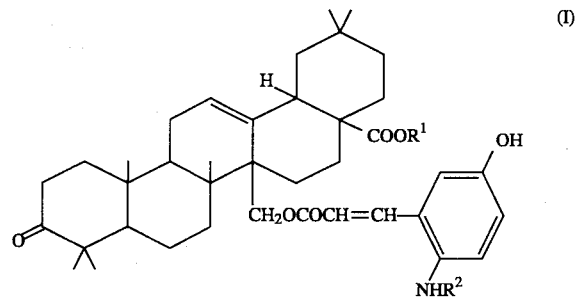

wherein $R^1$ is hydrogen or metabolic ester residue; and $R^2$ is hydrogen or $-R^3-R^4$ wherein $R^3$ is $-SO_3-$, $-CH_2COO-$, $-COCOO-$, or $-COR^5COO-$ ($R^5$ is lower alkylene or lower alkenylene), and $R^4$ is hydrogen or metabolic ester residue or a pharmaceutically acceptable salt thereof, which have anti-endothelin activities and are useful in prophylaxis and treatment of diseases caused by excessive secretion of endothelin.

6 Claims, No Drawings

TRITERPENE DERIVATIVES AND ENDOTHELIN-RECEPTOR ANTAGONISTS CONTAINING THE SAME

FIELD OF THE INVENTION

This invention relates to useful compounds in the field of medicament and the use thereof, more specifically, to novel triterpene derivatives which can compete with endothelin for its receptors and are useful in the prophylaxis and treatment of diseases caused by excessive secretion of endothelin, and to pharmaceutical compositions containing the same.

BACKGROUND OF THE INVENTION

Endothelin, which has been disclosed by M. Yanagisawa et al., Nature, 332, pp. 411, 1988, is an endothelium-derived vasoconstrictor peptide composed of 21 amino acids and is considered to act on various organs and tissues including blood vessel, trachea and the like through activation of specific receptors on cell membrane. It has been supposed that this peptide can cause contradiction of smooth muscles and that an excessive secretion thereof may lead to various circulatory diseases such as hypertension, coronary ischemia, encephalopathy, nephropathy, circulation failure of various organs, and asthma.

It has been reported that $TXA_2$-receptor antagonists and inhibitors of $TXA_2$-synthetic enzyme and the like can prevent the increase in intracellular calcium-ion level following the excessive secretion of endothelin. However, there have been no reports about specific antagonists against endothelin so far and, therefore, the development of substances capable of inhibiting various actions of endothelin has been demanded. Under the conditions, the present inventors had made intensive study and found that certain triterpene derivatives extracted from *Myrica cerifera* L. can specifically compete with endothelin for its receptors (PCT/JP/91/01707, WO92/12991, U.S. Pat. No. 5,248,807).

The present inventors have made continuous efforts with purposes of developing more endothelin antagonists with higher activity and now found that certain novel triterpene derivatives are useful to achieve said purposes.

Thus, the present invention provides a compound of the formula (I)

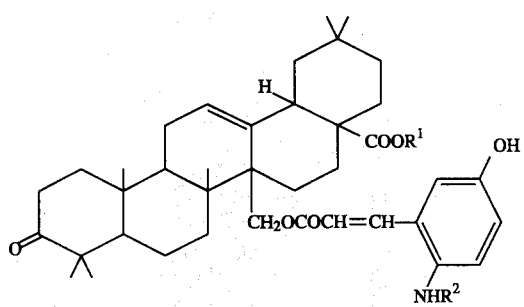

wherein $R^1$ is hydrogen or a metabolic ester residue; $R^2$ is hydrogen or $-R^3-R^4$ wherein $R^3$ is $-SO_3-$, $-CH_2COO-$, $-COCOO-$, or $-COR^5COO-$ ($R^5$ is lower alkylene or lower alkenylene), $R^4$ is hydrogen or lower alkyl or a pharmaceutically acceptable salt thereof.

Although all compounds of formula (I) are highly active endothelin antagonists and useful for purposes of the present invention, those wherein $R^1$ is hydrogen are preferable and those wherein $R^1$ is hydrogen and $R^2$ is $-COCH=CHCO_2H$ are more preferable.

For purposes of the present invention, as disclosed and claimed herein, the following terms are defined below.

The term "metabolic ester-residue" in definition fox $R^1$ means independently an ester-residue which decomposes to reproduce biologically active carboxylic acid in a living body. Examples of metabolic ester-residue include (1-acyloxy) lower alkyl such as picvaloyloxymethyl, acetoxymethyl, 1-acetoxyethyl and the like; (1-alkoxycarbonyloxy) lower alkyl such as 1-(ethoxycarbonyloxy)ethyl, 1-(isopropoxycarbonyloxy)ethyl and the like; and (5-methyl-1,3-dioxolene-4-yl)methyl and the like.

The term "lower alkylene" means $C_1$–$C_6$ alkylene shown by the formula $-(CH_2)_n-$ ($n=1-6$), preferably $C_1$–$C_4$ alkylene such as methylene, ethylene, trimethylene and the like.

The term "lower alkenylene" means $C_1$–$C_6$ alkenylene such as vinylene, propenylen, butenylene and the like. Preferable groups are those shown by the formula $-(CH=CH)_m-$ ($m=1-3$).

The term "lower alkyl" in definition for $R^4$ means straight or branched $C_1$–$C_6$ alkyl such as methyl, ethyl, propyl, t-Butyl. The compounds (I) of the present invention may form salts with alkali metals (sodium, potassium etc.), alkaline earth metals (calcium, magnesium etc.), ammonium or an organic base (triethylammonium, trimethylammonium etc.).

The compounds (I) of the present invention may form salts with inorganic acids (HCl, $H_2SO_4$ etc.), organic acids (benzenesulfonic acid, p-toluene sulfonic acid etc.) and the like.

The compounds (I) of the present invention having endothelin receptor antagonistic activities are novel. Although the preparation of them can be carried out using methods known in the art, it can be done efficiently according to the following method.

Thus, the compounds (I) can be prepared by reacting a compound of the formula (V):

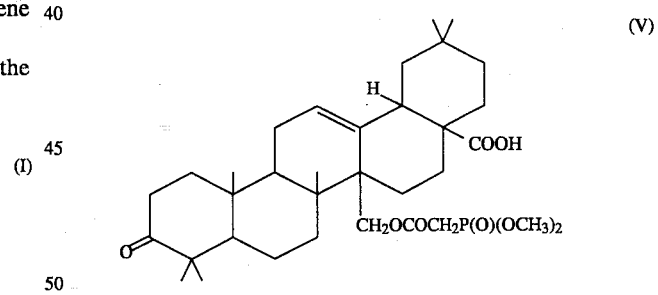

which has been disclosed in WO92/12991 with a corresponding aldehyde under reaction conditions of Horner-Emmons reaction in the presence of an amine such as triethylamine together with cesium carbonate or lithium bromide. The starting compound (V) can be derived from a substance which is obtainable from *Myrica cerifera* by extraction in a similar manner to that described in WO92/12991. Briefly, twigs of the plant are extracted for several days at room temperature with a polar solvent (e.g., alcohol such as methanol, ethanol, isopropanol, n-butanol, sec-butanol, tert-butanol; acetone; or acetonitrile). The resultant solution is further extracted with a water-immiscible organic solvent (e.g., chlorinated hydrocarbon such as chloroform, dichloromethane; ethyl acetate; or n-butanol) and the extract is chromatographed on silica gel. The isolated substance is then subjected to chemical modification to obtain Myricerone of the formula (IV):

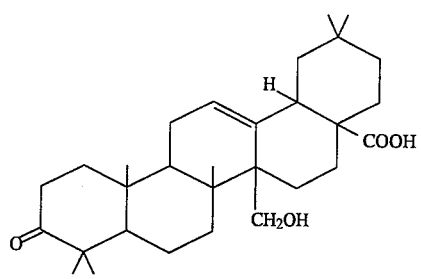

(IV)

The compound (V) is obtained by reacting the compound (IV) with dimethylphosphonoacetic acid.

The compound (V) is then reacted with an aldehyde of the formula (III):

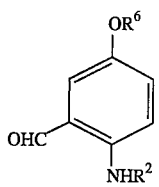

(III)

wherein $R^2$ is as defined above and $R^6$ is t-butoxycarbonyl (hereinafter, referred to as Boc) or hydrogen under the reaction condition for Horner-Emmons reaction. The condensation product is deprotected and/or chemically modified to give the compound (I) of the present invention.

The Horner-Emmons reaction can be effected in either of following two methods.

Method 1

Carboxylic acids of the formula (I), for example, those wherein $R^2$ is —COCH=CHCO$_2$H, can be prepared directly by reacting a compound (V) with an aldehyde (III) having desired substituent, for example, a compound (III) wherein $R^2$ is —COCH=CHCO$_2$Me and $R^6$ is hydrogen, in an appropriate solvent such as dimethylformamide (DMF), dimethyl sulfoxide (DMSO), acetonitrile or the like in the presence of diazabicycloundecene (DBU), lithium chloride etc. at 0°–50° C., preferably at room temperature for 0.1–24 hr, preferably for 0.5–2 hr, extracting the reaction mixture with ethyl acetate, methylene chloride etc. to obtain methyl ester, and hydrolyzing said methyl ester.

Method 2

Method 2 has the advantage that various derivatives of compound (I) can be prepared readily. Amines of the formula (I) wherein $R^2$ is hydrogen can be prepared by reacting a compound (V) with an aldehyde (III) wherein $R^2$ is hydrogen and $R^6$ is Boc in a manner similar to that described in method 1, treating the resultant condensation product with anisole and trifluoroacetic acid at 0°–50° C., preferably at room temperature for 0.1–24 hr, preferably for 0.5–2 hr for deprotection, and purifying the product by means of, for example, column chromatography using silica gel. The resultant amines are further used in the production of various derivatives.

As is clear from the experimental results shown below, the compounds (I) of the present invention have endothelin receptor antagonistic activity and can be used not only in prophylaxis and treatment of circulatory diseases such as vasoconstriction, hypertension or the like, but also in reduction of renal toxicity of immunosurpressant cyclosporin.

For clinical application, the compounds of the present invention can be formulated into appropriate formulations for oral, parenteral or anal administration together with conventional carriers, diluents, excipients or the like according to general methods.

Although appropriate daily dosage of the compound of the present invention varies depending upon various factors such as the intended therapeutical effects, administration route, age and body weight of the patient, it can generally be between 10 mg–2 g, preferably 50 mg–1 g on oral administration, and 5 mg–2 g, preferably 50 mg–1 g on parenteral administration, in 1–4 divisions for an adult.

The following Examples are provided to further illustrate the present invention and are not to be construed as limiting thereof.

Preparation 1

Preparation of Myricerol (4)

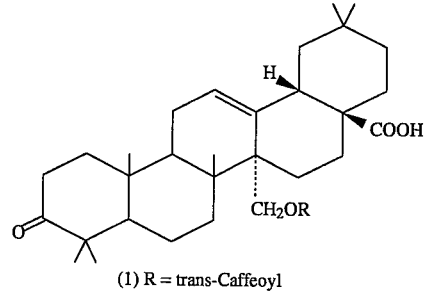

(1) R = trans-Caffeoyl

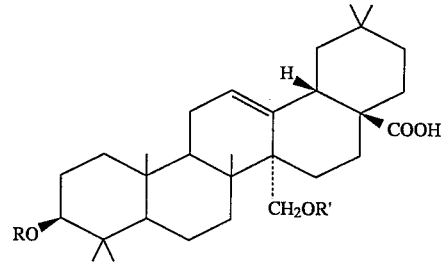

(2) R = H, R' = trans-Caffeoyl
(3) R = R' = trans-Caffeoyl
(4) R = R' = H

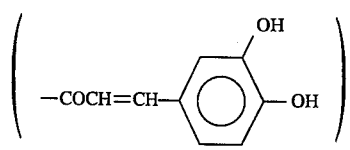

1) Twigs (170 kg) of *Myrica cerifera* were extracted with methanol at room temperature to obtain extract (9.6 kg). The extract was divided into portions (500 g each) and partitioned between ethyl acetate (1.5 l) and water (1 l), separately. The resultant ethyl acetate solution (2.4 kg in total) was divided into portions (200 g each) and separately chromatographed on ODS silica gel (Chromatorex ODS, Fuji-Division Chemical Ltd., 800 g) eluting with methanol/water (85:15) to obtain fraction (a) (136.4 g in total) containing compounds (1) and (2) and fraction (b) (226.5 g in total) containing mainly compound (3).

The fraction (a) was subjected to acetylation followed by separation by means of centrifuging liquid-liquid partition chromatography (eluent: n-hexane/toluene/methanol/water, 70:30:35:15) to yield a fraction (171 g) containing acetylated compound (1) and that containing acetylated compound (2) (.56 g). From the former fraction, acetylated compound (1) (23 g) was obtained.

The acetylated compound (2) (56 g) was halved and the each portion was dissolved in 10 % methanolic aqueous potassium hydroxide solution (700 ml, water content, 10 %). The solution was heated to reflux under an atmosphere of argon for 72 hr. After the addition of water (100 ml), the mixture was distilled under reduced pressure to remove methanol, adjusted to pH 6 with dil. HCl, and extracted with ethyl acetate (300 ml) (×3). The ethyl acetate solution was washed with water and distilled to remove ethyl acetate. To the residue was added methanol and the resultant precipitates were filtered off. The mother liquid was chromatographed on ODS silica gel eluting with methanol/water (85:15) and crystals separated out were filtered off. The first and second crops were combined and recrystallized from methanol to yield compound (4) (13.5 g).

Fraction (b) (226 g) containing mainly compound (3) was treated with an alkali in the same manner as above to yield compound (4) (43 g). M.p. 250°–251° C.
Myricerol (4)

$[\alpha]_D^{25}$ +65.3° (CHCl$_3$).

MS m/z 472(C$_{30}$H$_{48}$O$_4$).

IR(CHCl$_3$): 3504, 1695cm$^{-1}$.

$^1$H NHR(CDCl$_3$) δ: 5.85(1H, br-t, H-12), 3.78(1H, d, J=12.2 Hz, H-27), 3.19(1H, d, J=12.2 Hz, H-27), 3.22(1H, dd, J=15.6, 5.2 Hz, H-3), 2.93(1H, dd, J=14.0, 4.6 Hz, H-18), 0.98, 0.96, 0.91, 0.88, 0.76, 0.71(each 3H, s, H-23, H-24, H-25, H-26, H-29, H-30 ).

$^{13}$C NMR(CDCl$_3$) δ: 38.1(C-1), 26.9(C-2), 78.8(C-3), 38.7(C-4), 54.9(C-5), 18.2(C-6), 32.3(C-7), 39.8(C-8), 48.4(C-9), 37.1(C-10), 24.1(C-11), 129.5(C-12), 137.9(C-13), 47.5(C-14), 24.5(C-15), 22.5(C-16), 46.0(C-17), 40.5(C-18), 45.0(C.19), 30.8(C-20), 33.5(C-21), 32.5(C-22), 28.0(C-23), 15.8(C-24), 15.5(C-25), 18.3(C-26), 62.9(C-27), 181.4(C-28), 33.0(C-29), 23.8(C-30).

2) Alternatively, the ethyl acetate-soluble fraction (1.6 kg) prepared from branches (100 kg) of *Myrica cerifera* in a similar manner as that described in 1) above was chromatographed on silica gel (eluent:methanol/water, 85:15) and fractions containing compound (1) (7 g) and succeeding fractions containing a mixture (142 g) of compounds (2) and (3) were collected. The latter fractions were treated with an alkali in the same manner as above to yield crude crystals of compound (4), which was recrystallized to yield compound (4) (36 g).

Preparation 2

Preparation of Horner-Emmons Reagent (Compound V).

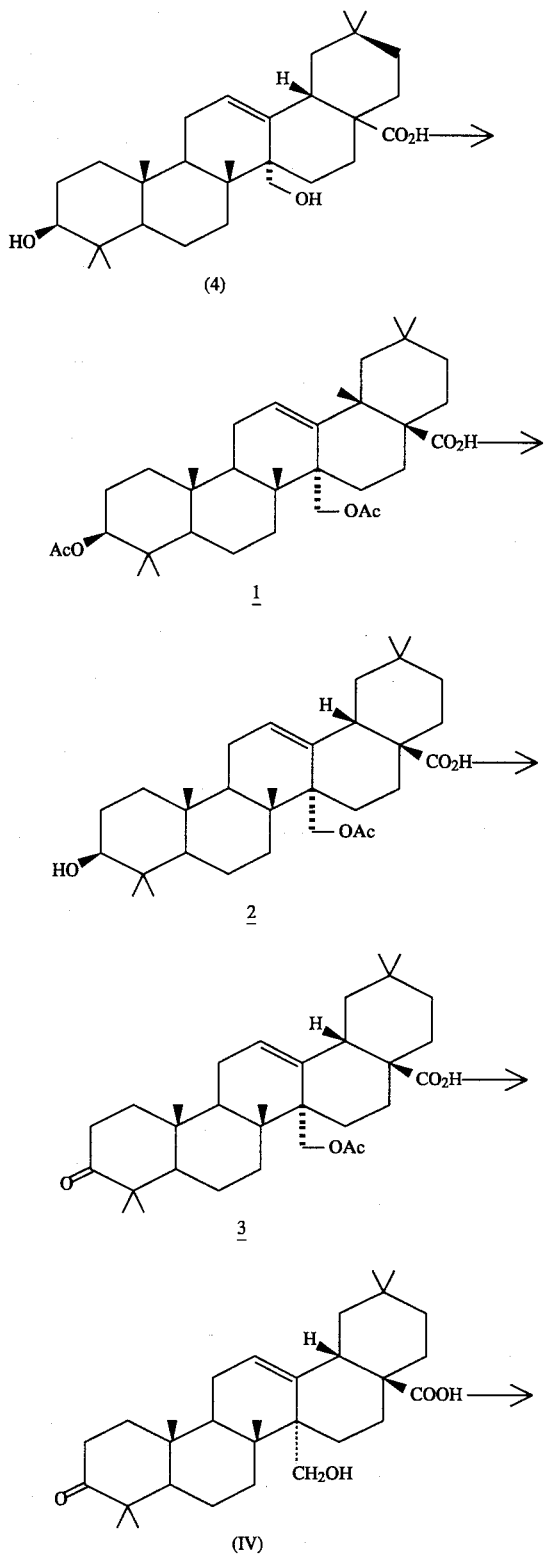

-continued

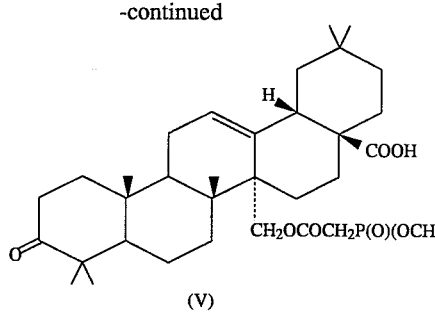

(V)

1) Preparation of Compound 1

To a solution of Myricerol (4) (10.19 g, 21.55 mmole) prepared in Preparation 1 in pyridine (80 ml) acetic anhydride (80 ml, 0.86 mole) is added dropwise at room temperature under an atmosphere of nitrogen over 10 min and the mixture stirred for 3.5 hr at room temperature. After cooling to 0° C., to the mixture is added dropwise methanol (69 ml, 1.70 mole) over 5 min. The mixture is stirred for 30 min at room temperature and poured into a mixture of ice-cooled conc. HCl (90 ml)/water (200 ml)/methylene chloride (400 ml). After separation of organic layer, aqueous layer is extracted with methylene chloride (400 ml). Each organic layer is washed with 1N HCl (300 ml), a brine (300 ml) (×2), dried over anhydrous magnesium sulfate, and concentrated to yield compound 1 as a crude product (12.0 g, 21.55 mmole, yield 100 %). M.p., 185°–186° C.

Compound 1

$^1$H NMR(CDCl$_3$) δppm: 0.72(s, 3H), 0.84(s, 3H), 0.87(s, 3H), 0.86(s, 3H), 0.93(s, 6H), 0.8–2.0(m, 22H), 2.03(s, 3H), 2.05(s, 3H), 2.88(dd, J=4.6 Hz, J=13.8 Hz, 1H), 4.04(ABq, Apart, J=12.7 Hz, 1H), 4.16(ABq, Bpart, J=12.7 Hz, 1H), 4.47(dd, J=6.6 Hz, J=9.4 Hz, 1H), 5.57(br s, 1H)

IR(CHCl$_3$): 1718, 1690cm$^{-1}$.

2) Preparation of Compound 2

To diacetate 1 (12.0 g, 21.55 mmole) is added 5% KOH solution in methanol (300 mi, water content, 5%) at room temperature under an atmosphere of nitrogen. The mixture is stirred for 2 hr at room temperature, cooled to 0° C., neutralized with 4N HCl (60 ml) and distilled under reduced pressure to remove methanol. The residue is dissolved in ice-cooled water (400 ml)/ethyl acetate (600 ml). After separation of organic layer, aqueous layer is extracted with methylene chloride (200 ml). Each organic layer is washed with brine (400 ml), dried over anhydrous magnesium sulfate, and concentrated. The residue is dissolved in tetrahydrofuran (THF) (50 ml). After addition of silica gel (50 g), the mixture is concentrated and purified by the use of column chromatography (SiO$_2$, 500 g; methylene chloride→ethyl acetate/methyl acetate (1:4)→ethyl acetate) to yield the objective compound 2 ( 6.38 g, 12.40 mmole, yield 58%). M.p., 257°–258° C.; [α]$_D$+103.5° (C 1.0/CHCl$_3$).

Compound 2

$^1$HNMR (CDCl$_3$) δppm: 0.72(s, 3H), 0.76(s, 3H), 0.87(s, 3H), 0.90(s, 3H), 0.93(s, 3H), 0.98(s, 3H), 0.9–2.0(m, 22H), 2.02(s, 3H), 2.88(dd, J=4.2 Hz, J=13.6 Hz, 1H), 3.22(dd, J=5.4 Hz, J=10.0 Hz, 1H), 4.05(ABq, Apart, J=12.4 Hz, 1H), 4.17(ABq, Bpart, J=12.4 Hz, 1H), 5.57(t, J=3.1 Hz, 1H).

IR(CHCl$_3$): 3510, 1722, 1692cm$^{-1}$.

$^{13}$C NMR(CDCl$_3$) δppm: 15.5, 15.6, 18.2, 18.3, 21.3, 22.7, 23.4, 23.6.23.8, 27.0, 28.0, 30.6, 32.4, 33.0, 33.0, 33.6, 37.2, 38.5, 38.7, 39.9, 40.7, 44.9, 44.9, 46.1, 48.7, 55.2, 66.3, 78.8, 127.2, 137.2, 171.1, 182.1.

3) Preparation of Compound 3

A mixture of compound 2 (18.13 g, 35.23 mmole ) and chloroform (600 ml) is diluted with acetone (300 ml). To the resultant solution is added dropwise Jones reagent (CrO$_5$/H$_2$SO$_4$, about 2.43M sulfuric acid solution, 21.75 ml, 52.85 mmole) at room temperature under an atmosphere of nitrogen and the mixture was stirred for 30 min at the same temperature. To the mixture is added dropwise methanol (42.94 ml, 1.06 mole) and stirred for 20 min at room temperature. The reaction mixture is poured into water (400 ml) and extracted with chloroform (800 ml) (×2). The organic layer is washed with water (400 ml), dried over anhydrous magnesium sulfate and concentrated to obtain crude product (17.39 g, 33.92 mmole, yield 96%). [α]$_D$+108.5° (C 1.0/CHCl$_3$).

Compound 3

$^1$HNMR (CDCl$_3$) δppm: 0.78(s, 3H), 0.88(s, 3H), 0.94(s, 3H), 1.02 (s, 3H), 1.03(s, 3H), 1.08(s, 3H), 0.9–2.0(m, 20H), 2.01(s, 3H), 2.3–2.7(m, 2H), 2.90(dd, J=4.2 Hz, J=13.6 Hz, 1H), 4.05(ABq, Apart, J=12.6 Hz, 1H), 4.20(ABq, Bpart, J=12.6 Hz, 1H), 5.59(br s, 1H).

IR(CHCl$_3$): 1725, 1696cm$^{-1}$.

$^{13}$C NMR(CDCl$_3$) δppm: 15.2, 18.1, 19.5, 21.2, 21.4, 22.6, 23.3, 23.6, 23.8.26.4, 30.6, 32.0, 32.3, 32.4, 33.5, 34.0, 36.9, 39.0, 39.8, 40.7, 44.7, 45.0, 46.3, 47.4, 47.9, 55.1, 65.9, 127.0, 137.0, 170.8, 183.7, 217.4.

4) Preparation of Compound (IV) (Myricerone)

To compound 3 (17.38 g, 33.9 mmole) is added 5% KOH solution (870 ml, water content, 5%) in methanol and the mixture is stirred at 65° C. for 3 hr, cooled to room temperature and distilled under reduced pressure to remove methanol until white crystals precipitates. The residue is acidified with ice-cooled 4N HCl (200 ml)/methylene chloride (600 ml) and the organic layer separated. The aqueous layer is extracted with methylene chloride (300 ml) (×2). Each organic layer is washed with water (400 ml) (×2) dried over anhydrous magnesium sulfate and purified with chromatography (SiO$_2$, 140 g; methylene chloride→ethyl acetate/methylene chloride (1:9→1:6→1:4) to yield the objective compound (IV) (13.0 g, 27.62 mmole, yield 81%)

M.p., 226°–227° C.; [α]$_D$+91.3° (C 1.0/CHCl$_3$).

Compound (IV)

$^1$HNMR (CDCl$_3$) δppm: 0.76(s, 3H), 0.92(s, 3H), 0.97(s, 3H), 1.01(s, 6H), 1.08(s, 3H), 1.0–2.1(m, 20H), 2.3–2.6(m, 2H), 2.94(dd, J=4.5 Hz, J=13.5 Hz, 1H), 3.24(ABq, Apart, J=12.6 Hz, 1H), 3.78(ABq, Bpart, J=11.8 Hz, 1H), 5.87(br s, 1H). IR(CHC$_{13}$): 3510, 1696cm$^{-1}$.

$^{13}$C NMR(CDCl$_3$) δppm: 15.5, 18.3, 19.5, 21.3, 22.4, 23.8, 24.1, 24.4, 26.5, 30.8, 32.0, 32.2, 33.0, 33.5, 34.0, 36.8, 38.7, 39.7, 40.4, 44.9, 46.2, 47.3, 47.5, 47.6, 54.7, 63.1, 129.4, 137.7, 183.4, 217.4.

5) Preparation of Compound (V)

To a solution of dimethylphosphonoacetic acid (7.07 g, 42.1 mmole) in methylene chloride (100 ml) is added thionyl chloride (9.21 ml, 126 mmole) at room temperature under an atmosphere of nitrogen, and the mixture stirred for 4 hr at room temperature and concentrated to obtain acid chloride (7.85 g).

To a solution of compound (IV) (6.60 g, 14.0 mmole) in methylene chloride (70 ml) is added dropwise pyridine (4.53 ml, 56 mmole) at −78° C. under an atmosphere of nitrogen, while the inner temperature rises to −73° C. To the mixture is added dropwise a solution of the acid chloride (7.85 g, 14.0 mmole) prepared above in methylene chloride (70 ml) over 25 min, while the inner temperature rises to −68° C. After stirring at −75° C. for 40 min, solvent was evaporated off under a reduced pressure. The residue is suspended in THF (84 ml) and cooled to 0° C. To the suspension is added 2N NaOH (14 ml, 28 mmole) and the mixture stirred at 0° C. for 1 hr. The reaction mixture is poured into ice-cooled 1N HCl (50 ml)/ethyl acetate (200 ml) and the organic layer is separated. The aqueous layer is extracted with ethyl acetate (150 ml) (×2). After the each organic layer is washed with a brine (100 ml)(×2), they are combined, dried over anhydrous magnesium sulfate and concentrated. The residue was purified by the use of column chromatography (SiO$_2$, 150 g; ethyl acetate/n-hexane (1:1)→ethyl acetate→chloroform/methanol (100:1→50:1→21:1) to give the objective compound (V) (7.43 g, 11.97 mmole, yield 85%). M.p., 110°–113° C.; $[\alpha]_{D22}$+83.9° (C 1.0/CHCl$_3$).

Compound (V)

$^1$HNMR (CDCl$_3$) δppm: 0.80(s, 3H), 0.89(s, 3H), 0.94(s, 3H), 1.02(s, 3H), 1.04(s, 3H), 1.08(s, 3H), 1.0–2.0(m, 20H), 2.3–2.7(m, 2H), 2.8–3.0(m, 1H), 2.95(d, $^2J_{PH}$=22.0 Hz, 2H), 3.78(s, 3H), 3.83(s, 3H), 4.13(ABq, Apart, J=12.9 Hz, 1H), 4.32(ABq, Bpart, J=12.9 Hz, 1H), 5.60(br s, 1H).

IR(CHCl$_3$): 2944, 1728, 1696, 1263cm$^-$.

$_{13}$C NMR(CDCl$_3$) δppm: 15.3, 18.0, 19.5, 21.4, 22.7, 22.8, 23.5, 23.7.26.5, 30.6, 32.2, 32.4, 32.8, 32.9, 33.6, 34.0, 34.9, 37.0, 39.0, 39.9, 40.8, 45.3, 46.3, 46.4(d, $^1J_{CP}$=144 Hz), 47.4, 53.1(d, $^2J_{COP}$=6.4 Hz), 53.2(d, $^2J_{COP}$=6.4 Hz), 66.8, 127.4, 137.0, 165.3(d, $^2J_{COP}$=6.4 Hz), 183.2, 217.3.

Preparation 3

Preparation of Aldehyde [III]

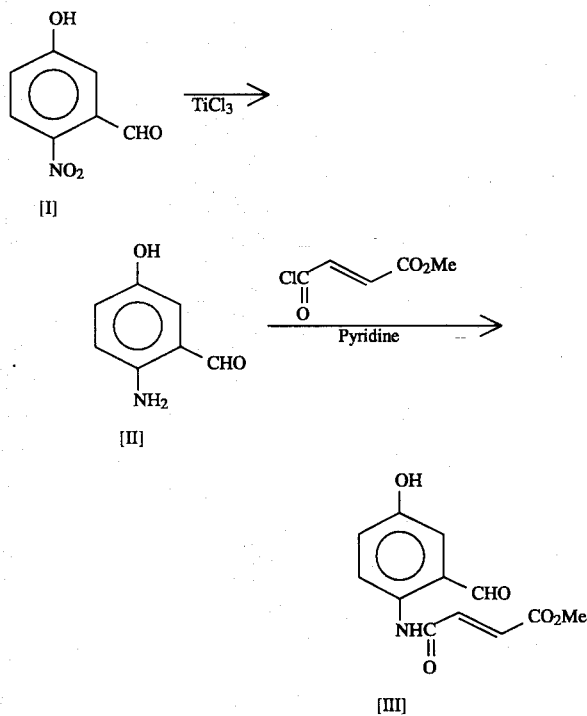

Aldehyde [III] was prepared by the procedure developed by Somei et al., Chem. Pharm. Bull. 28: 2515 (1980).

To a solution of hydroxynitrobenzaldehyde [I] (1 g) in acetic acid/water (1:1) (20 ml) is added aqueous solution (25 ml) of titanium trichloride and the mixture stirred for 10 min at room temperature. The reaction mixture is poured into water/ethyl acetate. The aqueous layer is adjusted to pH 8 with sodium carbonate and extracted with ethyl acetate. Ethyl acetate extract is dried over anhydrous magnesium sulfate and concentrated to about 20 ml to obtain a solution of compound [II] in ethyl acetate.

To the solution are added pyridine (0.46 ml) under ice-cooling and 3-methoxycarbonylacrylic acid chloride (442 mg). After stirring at 0° C. for 30 min, the reaction mixture is extracted with ethyl acetate. The extract is concentrated and the resultant solid precipitates are separated out, which are filtered off to obtain the objective aldehyde [III](432 mg, yield 29%) as powder.

Compound [III]

$^1$HNMR (CDCl$_3$+CD$_3$OD) δppm: 3.85(s, 3H), 6.91(d, 1H, J=15.4 Hz), 7.12(d, 1H, J=15.4 Hz), 7.14(d, 1H, J=2.8 Hz), 7.18(dd, 1H, J=8.8, 2.8 Hz), 8.58(d, 1H, J=8.8 Hz), 9.86(s, 1H).

Example 1

Preparation of Compound (I) (R$^1$=H; R$^2$=—C(O)CH=CHCO$_2$H)

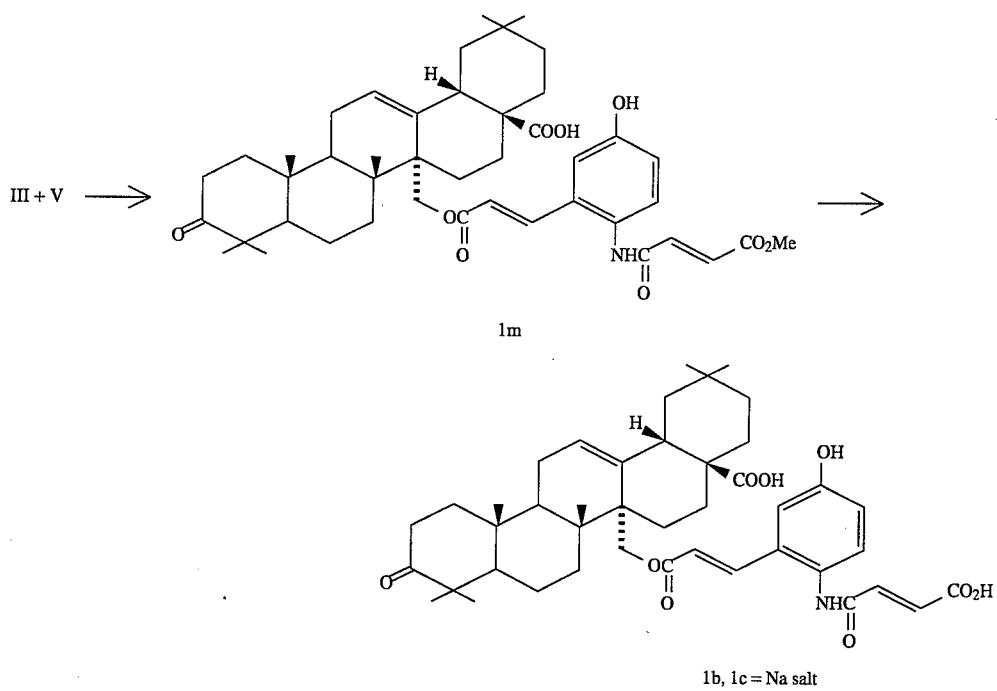

1m 1b, 1c = Na salt

1) Preparation of Compound 1m (Condensation of Compounds [III] and (V))

To a solution of Horner-Emmons reagent (Compound (V)) (621 mg, 1 mmole) prepared in Preparation 2 above and aldehyde [III] (299 mg, 1.2 mmole) in dimethylformamide (6 ml) are added diazabicycloundecene (DBU) (0.358 ml) and lithium chloride (93 mg), and the mixture stirred at room temperature for 1.5 hr. The reaction mixture is extracted with ethyl acetate and chromatographed on silica gel (eluent:chloroform/methanol) to yield compound 1m (670 mg, yield 90%).

Compound 1 m $^1$HNMR (CDCl$_3$) δppm: 0.83(s, 3H), 0.84(s, 3H), 0.93(s, 3H), 1.03(s, 3H), 1.04(s, 3H), 1.07(s, 3H), 1.0–2.1(m, 20H), 2.2–2.8(m, 2H), 2.8–3.0(m, 1H), 3.84(s, 3H), 4.16, 4.40(ABq, 2H, J=13.0 Hz), 5.61(br s, 1H), 6.27(d, 1H, J=16.0 Hz), 6.90(dd, 1H, J=8.8, 2.8 Hz), 6.94(d, 1H, J=15.2 Hz), 7.07(d, 1H, J=2.8 Hz), 7.21(d, 1H, J=15.2 Hz), 7.44(d, 1H, J=8.8 Hz), 7.74(d, 1H, J=16.0 Hz).

Compound 1 m which is the precursor of compound 1 b is also a compound of the present invention.

2) Preparation of Compound 1b

To a solution of methyl ester 1m (5 mg, 6.6 µmole) in methanol (300 µl) is added 1N NaOH (100 µl). The mixture is stirred at room temperature for 1.5 hr and extracted with ethyl acetate. The extract is concentrated under reduced pressure. The residue is purified with chromatography on silica gel (eluent: ethyl acetate/acetic acid/water, 30:1:1) to yield compound 1b (3.5 mg, yield 73

3) Preparation of Compound 1c

To a suspension of compound 1b prepared above (21.9 mg, 0.03 mmole) in water (1.2 ml) is added 0.1 N NaOH (600 µl) and the resultant solution is freeze-dried to give the disodium salt (Compound 1c) (21.5 mg, yield 93%).

Example 2

Preparation of Compound (I) ($R^1$=H; $R^2$=H)

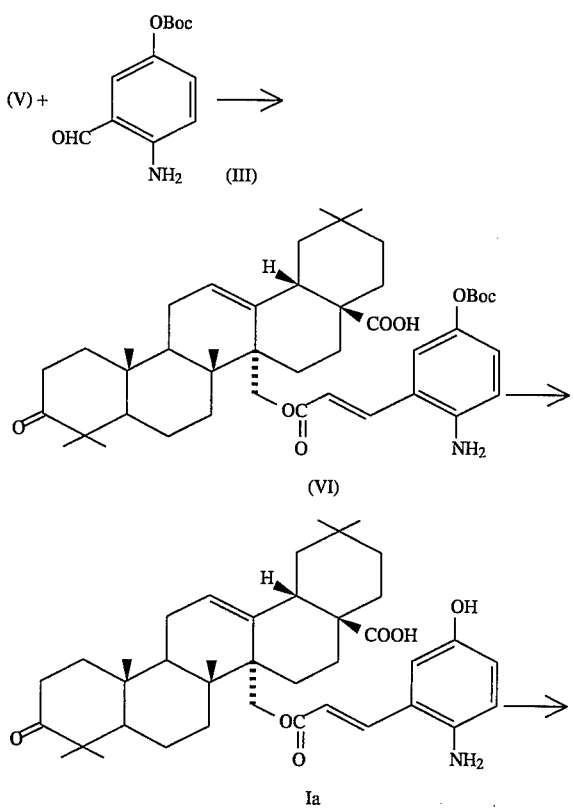

-continued

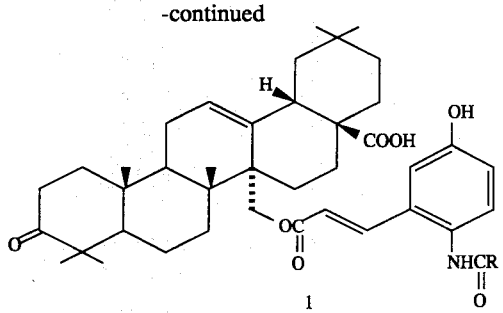

1) Alternative Preparation of 2-Amino-5-hydroxy Compound (1)

i) Preparation of Aldehyde (III)

According to the procedure of E. Georgavakis et al., Helv. Chim. Acta., 62:234 (1979), crude 2-amino-5-hydroxybenzaldehyde was prepared. 2-amino-5-hydroxybenzaldehyde prepared from indazole (400 mg, 3.39 mmole) was dissolved in ethyl acetate (about 100 ml). To the solution are added triethylamine (2.36 g), di-tert-butyldicarbonate ((Boc)$_2$O) (37 g) and catalytic amount of dimethylaminopyridine (DMAP). The mixture is stirred for 1 hr at room temperature, extracted with chloroform, and chromatographed on silica gel (N-hexane/ethyl acetate, 4:1) to yield aldehyde (III) (454 mg, yield 56%).

Aldehyde (III)

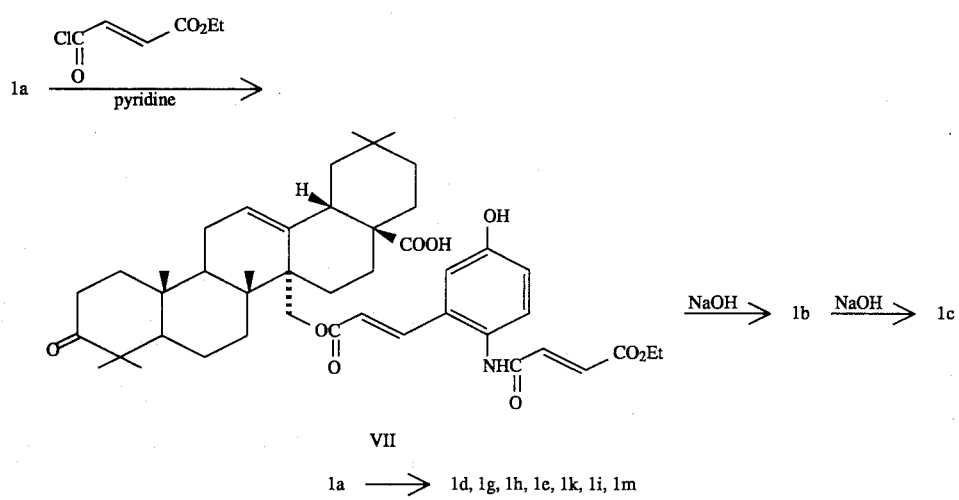

$^1$HNMR (CDCl$_3$) δppm: 1.56(s, 9H), 6.65(d, 1H, J=8.8 Hz), 7.12(dd, 1H, J=8.8, 2.8 Hz), 7.30(d, 1H, J=2.8 Hz), 9.82(s, 1H).

ii) Preparation of Hydroxy-protected Amine (VI)

To a solution of compound (V) (294 mg, 0.474 mmole) and aldehyde (III) (135 mg, 1.2 eq.) prepared above in isopropyl alcohol (4 ml) is added cesium carbonate (618 mg, 4 eq.). The mixture is stirred for 1.5 hr at room temperature, extracted with ethyl acetate, and concentrated. The residue, when purified with silica gel chromatography (hexane/ethyl acetate, 1: 1 ), gives the condensation product (VI) ( 350 mg, yield 93% ).

Compound (VI)

$^1$HNMR (CDCl$_3$) δppm: 0.83(s, 3H), 0.86(s, 3H), 0.93(s, 3H), 1.03(s, 3H), 1.03(s, 3H), 1.08(s, 3H), 1.57(s, 9H), 1.1–2.1 (m, 20H), 2.2–2.6(m, 2H), 2.8–3.0(m, 1H), 4.12, 4.42(ABq, 2H, J=11.8 Hz), 5.64(br s, 1H), 6.25(d, 1H, J=15.6 Hz ), 6.76(d, 1H, J=9.0 Hz), 7.04(dd, 1H, J=9.0, 2.6 Hz), 7.20(d, 1H, J=2.6 Hz), 7.75(d, 1H, J=15.6 Hz).

iii) Preparation of Amine 1a by Deprotection

To a solution of compound (VI) (330 mg, 0.45 mmole) in anisole (3 ml) is added trifluoroacetic acid (3.0 ml). The mixture is stirred for 2 hr at room temperature and concentrated under reduced pressure. The residue, when purified with silica gel chromatography (ethyl acetate), gives compound 1a (210 mg, yield 74%).

Example 3

Compounds 1b–1e, 1g–1i, and 1k were prepared using the compound 1a prepared in Example 2 as a starting material.

| Compound | R$^1$ | R$^2$ |
|---|---|---|
| 1b | H | COCH=CHCOOH (trans) |
| 1c | Na | COCH=CHCOONa (trans) |
| 1d | H | COCH=CHCOOH (cis) |
| 1g | H | COCOOH |
| 1h | H | COCH$_2$COOH |
| 1e | H | CO(CH$_2$)$_2$COOH |
| 1i | H | CO(CH$_2$)$_3$COOH |

-continued

| Compound | R¹ | R² |
|---|---|---|
| 1k | H | SO₃H |

1) Preparation of Compound 1b i) To a solution of compound 1a (10 mg) in methylene chloride (150 μl) is added pyridine (13 μl) and then 3-ethoxycarbonylacryloyl chloride (32 μl, 2 eq.) at −78° C. The reaction mixture is stirred at room temperature for 1 hr and extracted with ethyl acetate. The extract is concentrated under reduced pressure. The residue, when purified with silica gel chromatography (Chloroform/methanol, 50:1), gives compound (VII) (7.2 mg, yield 60%).

Compound (VII)

¹HNMR (CDCl₃+CD₃OD) δppm: 0.82(s, 3H), 0.86(s, 3H), 0.93(s, 3H), 1.04(s, 6H), 1.06(s, 3H), 1.34(t, 3H, J=7.2 Hz), 1.1–2.1(m, 20H), 2.2–2.7(m, 2H), 2.8–3.0(m, 1H), 4.28(q, 2H, J=7.2 Hz), 4.15, 4.40(ABq, 2H, J=13.2 Hz), 5.61(br s, 1H), 6.24(d, 1H, J=15.8 Hz), 6.89(dd, 1H, 8.6, 2.8 Hz), 6.94(d, 1H, J=15.4 Hz), 7.05(d, 1H, J=2.8 Hz), 7.20(d, 1H, J=15.4 Hz), 7.47(d, 1H, J=8.6 Hz), 7.74(d, 1H, J=15.8 Hz).

ii) To a solution of ethyl ester (VII) (5 mg, 6.6 μmole) in methanol (300 μl) is added 1N NaOH (100 μl). The mixture is stirred at room temperature for 1.5 hr and extracted with ethyl acetate and the extract concentrated under reduced pressure. The residue, when purified with silica gel chromatography (ethyl acetate/acetic acid/water, 30:1:1), gives compound 1b (3.5 mg, 73%).

2) Preparation of Compound 1c

To a suspension of compound 1b (21.9 mg, 0.03 mmole) prepared in 1) above in water (1.2 ml) is added 0.1N NaOH (600 μl) and the resultant solution is freeze-dried to yield disodium salt 1c (21.5 mg, yield 93%).

3) Preparation of Compound 1d

To a suspension of compound 1a (3.2 mg, 0.005 mmole) in methylene chloride (0.2 ml) are added maleic anhydride (1.0 mg, 0.01 mmole) and pyridine (0.8 μl, 0.01 mmole) at 0° C. under an atmosphere of nitrogen. The mixture is stirred for 1.5 hr at room temperature, diluted with ethyl acetate and poured into ice-cooled 1N HCl. The organic layer is separated and the aqueous layer is extracted with ethyl acetate. The organic layers are combined and washed with a brine, dried over anhydrous magnesium sulfate and concentrated. The residue, when purified with column chromatography (SiO₂, ethyl acetate→ethyl acetate/acetic acid/water (30:1:1)), gives compound 1d (3.32 mg, yield 91%).

4) Preparation of Compound 1e

To a suspension of compound 1a (3.2 mg, 0.005 mmole) in methylene chloride (0.2 ml) are added succinic anhydride (1.0 mg, 0.01 mmole) and pyridine (0.8 μl, 0.01 mmole) at 0° C. under an atmosphere of nitrogen. The mixture is dissolved in DMF (30 μl) and the resultant solution stirred for 1 hr at room temperature. After addition of catalytic amount of DMAP, the mixture is stirred for another 1 hr, diluted with ethyl acetate and poured into ice-cooled 1N HCl. The organic layer is separated and the aqueous layer is extracted with ethyl acetate. Each organic layer is washed with a brine, dried over anhydrous magnesium sulfate and concentrated. The residue was purified by column chromatography (SiO₂, ethyl acetate→ethyl acetate/acetic acid/water (30:1:1)) to give compound 1e (2.00 mg, yield 55%).

5) Preparation of Compound 1g

To a solution of compound 1a (11.6 mg) and pyridine (4.5 μl) in methylene chloride (0.2 ml) is added monomethyl oxalyl chloride (1.9 μl, 1.1 eq.) at −78° C. The mixture is stirred for 10 min at −40° C. and extracted and purified by chromatography to yield methyl ester (8.5 mg, 64%) of compound 1q. To a solution of methyl ester (7.4 mg) in methanol (0.3 ml) is added 1N NaOH (0.15 ml) and the mixture stirred for 2 hr at 0° C. The reaction mixture is extracted and purified by chromatography to give compound 1g (3.0 mg, 41%).

6) Preparation of Compound 1h i) To a suspension of compound 1a (6.3 mg, 0.01 mmole) in methylene chloride (0.3 ml) is added DMF (30 μl) to obtain a solution. To the solution are added pyridine (1.2 μl, 0.015 mmole) and 1M ethoxycarbonylacetyl chloride solution (11 μl, 0.011 mmole) in methylene chloride at −50° C. under an atmosphere of nitrogen. After stirring at −50° C. for 15 min, the mixture is diluted with ethyl acetate and poured into ice-cooled 1N HCl. The organic layer is separated and the aqueous layer is extracted with ethyl acetate. Each organic layer is washed with a brine, dried over anhydrous magnesium sulfate and concentrated. The residue was purified with column chromatography (SiO₂, ethyl acetate/n-hexane (2:1)→ethyl acetate) to give ethyl ester of compound 1h. (4.0 mg, yield 54%).

¹H NMR(CDCl₃) δppm: 0.81(s, 3H), 0.87(s, 3H), 0.94(s, 3H), 1.03(s, 6H), 1.07(s, 3H), 1.34(t, J=7.0 Hz, 3H), 1.0–2.1(m, 20H), 2.2–2.6(m, 2H), 2.8–3.0(m, 1H), 3.54(s, 2H), 4.30(q, J=7.0 Hz, 2H), 4.18(ABq, Apart, J=13.3 Hz, 1H), 4.39(ABq, Bpart, J=13.3 Hz, 1H), 6.28(d, J=15.8 Hz, 1H), 6.82(dd, J=2.6 Hz, 8.8 Hz, 1H), 6.99(d, J=1.6 Hz, 1H), 7.39(d, J=8.8 Hz, 1H), 7.75(d, J=15.2 Hz, 1H).

ii) To a solution of ethyl ester (4.0 mg, 0.00536 mmole) prepared in i) above in methanol (100 μl) is added 2N NaOH (50 μl, 0.10 mmole) at 0° C. under an atmosphere of nitrogen. The mixture is stirred for 30 min at 0° C. diluted with ethyl acetate and poured into ice-cooled 1N HCl. The organic layer is separated and the aqueous layer is extracted with ethyl acetate. Each organic layer is washed with a brine, dried over anhydrous magnesium sulfate and concentrated. The residue, when purified with column chromatography (SiO₂, chloroform/methanol (50:1→10:1)→ethyl acetate→ ethyl acetate/acetic acid/water (30:1:1)), gives compound 1h (1.9 mg, yield 50%).

7) Preparation of Compound 1i

To a solution of compound 1a (5.0 mg, 0.0079 mmole) in DMF (50 μl) are added pyridine (1.3 μl, 0.0158 mmole) and glutaric anhydride (1.4 mg, 0.0119 mmole) at 0° C. under nitrogen atmosphere. After stirring at room temperature for 16 hr, the mixture is diluted with ethyl acetate and poured into ice-cooled 1N HCl. The organic layer is separated and the aqueous layer is extracted with ethyl acetate. Each organic layer is washed with a brine, dried over anhydrous magnesium sulfate and concentrated. The residue was purified by column chromatography (SiO₂, chroloform/methanol (50:1)→(20:1)→(10:1)→(6:1)) to give compound 1i (3.0 mg, 51%).

8) Preparation of Compound 1k

To a solution of compound 1a. (29.5 mg, 0.0467 mmole) in DMF (0.5 ml) is added a complex of sulfur trioxide and trimethylamine (32.5 mg, 0.233 mmole) at room temperature under an atmosphere of nitrogen. After stirring at room temperature for 50 min, the mixture is concentrated and purified with column chromatography (SiO₂, ethyl acetate/ acetic acid/water (30:1:1)→(15:1:1)→(8:1:1)→(4:1:1) to give compound 1k (4.42 mg, yield 13%).

Example 4

Preparation of Compound in ($R^1$=H; $R^2$=CH$_2$COOH).

Compound 1n was prepared essentially in a similar way to that described in Example 2.

1) Preparation of Aldehyde i) To a solution of indazole (1.0 g, 8.3 mM) in methanol (10 μl) are added 28% solution of sodium methoxide in methanol (3.53 ml, 18.26 mmole) and bromoacetic acid (1.41 g, 9.96 mmole), and the mixture is heated to reflux for 2 hr. After addition of the same amount of sodium methoxide and bromoacetic acid, the mixture is heated to reflux for another 1 hr. This procedures of-addition are repeated two more times and the mixture is cooled to 0° C. After addition of ethyl acetate, the mixture is adjusted to pH 5 with 1N HCl. The organic layer is taken and the aqueous layer extracted with ethyl acetate. Each organic solution is washed with a brine, dried over anhydrous magnesium sulfate and concentrated. The residue, when purified with column chromatography (SiO$_2$, ethyl acetate→ethyl acetate/acetic acid/water, (40:1:1)→(30:1:1)→(8:1:1)), gives 1-carboxymethylindazole (487 mg, yield 33%). $^1$H NMR (DMSO) δppm: 5.27(s, 2H), 7.16(dd, J=7.0 Hz, J=8.0 Hz, 1H), 7.39(dd, J=7.0 Hz, J=8.0 Hz, 1H), 7.64(d, J=8.0 Hz, 1H), 7.77(d, J=8.0 Hz, 1H), 8.09(s, 1H).

ii) To a solution of 1-carboxymethylindazole (236 mg, 1.34 mmole) in THF (2 ml) is added a solution of diazomethane in diethyl ether until yellowish color does not fade away. The solution is concentrated and the residue is purified with column chromatography (SiO$_2$, ethyl acetate/hexane, (1:3)→(1:2)) to obtain 1-methoxycarboxymethylindazole (182 mg, yield 71%).

$^1$H NMR(CDCl$_3$) δppm: 3.75(s, 3H), 5.18(s, 2H), 7.19(ddd, J=1.0 Hz, J=6.0 Hz, J=8.0 Hz, 1H), 7.34(dd, J=1.0 Hz, J=8.0 Hz, 1H), 7.43(ddd, J=1.0 Hz, J=6.0 Hz, J=8.0 Hz, 1H), 7.76(dd, J=1.0 Hz, J=8.0 Hz, 1H), 8.07/s, 1H).

iii) 1-Methoxycarboxymethylindazole (100 mg, 0.526 mmole) is dissolved in dioxane (2ml) in a quartz photo apparatus and diluted with 0.1 N sulfuric acid (200 ml). After nitrogen gas is bubbled into the solution for 20 min, the reaction mixture is cooled to 0° C., and irradiated with a high pressure mercury lump (450 watt) for 20 min, and extracted with ethyl acetate (×2). The ethyl acetate extract is washed with a brine, dried over anhydrous magnesium sulfate and concentrated to yield 5hydroxy-2-methoxycarbonylmethylamino-benzaldehyde (ca. 8g).

$^1$H NMR(CDCl$_3$) δppm: 3.79(s, 3H), 4.03(s, 2H), 6.49(d, J=9.6 Hz, 1H), 7.02(d, J=2.8 Hz, 1H), 7.02(dd, J=2.8 Hz, J=9.6 Hz, 1H), 9.80(s, 1H).

iv) To ethyl acetate solution of crude product obtained in iii) above are added pyridine (85 μl, 1.05 mmole) and acetic anhydride (55 μl, 0.579 mmole) at 0° C. under an atmosphere of nitrogen. After stirring for 1 hr at 0° C. and for 15 min at room temperature, pyridine (425 μl, 5.25 mmole) and acetic anhydride (55 μl, 0.579 mmole) are added to the mixture. After the mixture is stirred for 20 min at room temperature, pyridine (425 μl, 5.25 mmole) and acetic anhydride (99 μl, 105 mmole) were added and stirring was continued for 1 hr at room temperature. The reaction mixture is poured into ice-cooled 1N HCl and extracted with ethyl acetate. The organic solution is washed with a brine, dried over anhydrous magnesium sulfate and concentrated. The residue was purified by column chromatography (SiO$_2$, 5 g; ethyl acetate/methylene chloride, 1:9) to give 5-acetoxy-2-methoxycarbonylmethylbenzaldehyde (89 mg, yield 67%).

$^1$H NMR(CDCl$_3$) δppm: 2.30(s, 3H), 3.80(s, 3H), 4.04(s, 2H), 6.55(d, J=9.0 Hz, 1H), 7.16(dd, J=2.6 Hz, J=9.0 Hz, 1H), 7.28(d, J=2.6 Hz, 1H), 8.63(br s, 1H), 9.82(s, 1H).

v) To a solution of aldehyde (6.0 mg, 0.024 mmole) in DMF (0.2 ml) are added compound (V) (12.4 mg, 0.02 mmole), DBU (12.0 μl, 0.08 mmole) and lithium chloride (3.4 mg, 0.08 mmole) at room temperature under an atmosphere of nitrogen and the mixture stirred for 1 hr at room temperature. The reaction mixture is diluted with ethyl acetate and poured into ice-cooled 1N HCl. The organic solution is taken and the aqueous layer extracted with ethyl acetate. Each organic layer is washed with a brine, dried over magnesium sulfate and concentrated. The residue, when purified with column chromatography (SiO$_2$; chloroform→chloroform/methanol, (100:1)→(50:1)), an addition product (i.e., methyl ester of compound 1n, $R^2$=CH$_2$CO$_2$Me)(10.5 mg, yield 70%).

$^1$H NMR(CDCl$_3$) δppm: 0.83(s, 3H), 0.87(s, 3H), 0.94(s, 3H), 1.02(s, 3H), 1.03(s, 3H), 1.08(s, 3H), 1.0–2.1(m, 20H), 2.29(s, 3H), 2.2–2.6(m, 2H), 2.8–3.0(m, 1H), 3.80(s, 3H), 3.94(s, 2H), 4.13(ABq, Apart, J=12.6 Hz, 1H), 4.43(ABq, Bpart, J=12.6 Hz, 1H), 5.69(br s, 1H), 6.27(d, J=15.6 Hz, 1H), 6.54(d, J=8.8 Hz, 1H), 7.01(dd, J=2.7 Hz, J=8.8 Hz, 1H), 7.11(d, J=2.7 Hz, 1H), 7.76(d, J=15.6 Hz, 1H).

vi) To a solution of the compound prepared above (9.7 mg, 0.013 mmole) in methanol (200 μl) is added 2N NaOH (100 μl, 0.20 mmole) at 0° C. under an atmosphere of nitrogen. After stirring for 1 hr at 0° C., the mixture is diluted with ethyl acetate and acidified with 1N HCl. The organic layer is separated and the aqueous layer extracted with ethyl acetate. Each organic layer is washed with a brine, dried over anhydrous magnesium sulfate and concentrated. The residue, when purified with column chromatography (SiO$_2$, chroloform/methanol (50:1)→(20:1)→ethyl acetate→ethyl acetate/acetic acid/water (30:1:1)), gives compound In (5.4 mg, yield 60%).

Spectral data of compounds (I) prepared in Examples are summarized below.

Compound 1a:

Rf: 0.35 (hexane/ethyl acetate; 1:1).

$^1$H NMR(CD$_3$OD) δppm: 0.87(s, 3H), 0.89(s, 3H), 0.95(s, 3H), 1.04(s, 3H), 1.07(s, 6H), 1.1–2.1(m, 20H), 2.3–2.6 (m, 2H), 2.9–3.1(m, 1H), 4.15, 4.50(ABq, 2H, J=12.6 Hz), 5.63(br s, 1H), 6.22(d, 1H, J=15.8 Hz), 6.70(d, 1H, J=1.5 Hz), 6.84(t, 1H, J=1.5 Hz), 7.86(d, 1H, J=15.8 Hz).

Compound 1b:

Rf: 0.65 (ethyl acetate/acetic acid/water; 30:1:1).

$^1$H NMR(CD$_3$OD) δppm: 0.85(s, 3H), 0.87(s, 3H), 0.94(s, 3H), 1.03(s, 6H), 1.05(s, 3H), 1.1–2.0(m, 20H), 2.3–2.6 (m, 2H), 2.8–3.0(m, 1H), 4.11, 4.49(ABq, 2H, J=12.6 Hz), 5.59(br s, 1H), 6.36(d, 1H, J=16.0 Hz), 6.84(d, 1H, J=15.6 Hz), 6.89(dd, 1H, J=8.6, 2.6 Hz), 7.12(d, 1H, J=2.6 Hz), 7.14 (d, 1H, J=8.6 Hz), 7.20(d, 1H, J=15.6 Hz), 7.66(d, 1H, J=16.0 Hz ).

Compound 1c:

$^1$NMR δppm (D$_2$O) DSS(Me$_3$SiCH$_2$CH$_2$CH$_2$SO$_3$Na) standard, 0.73 ( s, 3H), 0.80(s, 3H) 0.87(s, 3H), 0.97(s, 3H), 1.00(s, 6H), 1.1–2.0(m, 20H) 2.2–2.6(m, 2H), 2.7–3.0(m, 1H), 4.05, 4.41(ABq, 2H, J=12.4 Hz), 5.58(br s, 1H), 6.34(d, 1H, J=16.0 Hz), 6.87, 6.92(ABq, 2H, J=16.0 Hz), 7.00(dd, 1H, J=8.6, 2.0 Hz), 7.19(d, 1H, J=8.6 Hz), 7.21(d, 1H, J=2.0 Hz), 7.58(d, 1H, J=16.0 Hz).

Compound 1d:

Rf: 0.67 (ethyl acetate/acetic acid/water; 30:1:1).

$^1$H NMR (CD$_3$OD) δppm: 0.85(s, 3H), 0.87(s, 3H), 0.95(s, 3H), 1.03(s, 3H), 1.05(s, 6H), 1.0–2.0(m, 20H), 2.2–2.6(m, 2H), 2.8–3.0(m, 1H), 4.12(ABq, A part, J=12.5

Hz, 1H), 4.48(ABq, B part, J=12.5 Hz, 1H), 5.62(br s, 1H), 6.35(d, J=15.8 Hz, 1H), 6.40(d, J=12.4 Hz, 1H), 6.49(d, J=12.4 Hz, 1H), 6.88(dd, J=2.8 Hz, J=8.8 Hz, 1H), 7.11(d, J=2.8 Hz, 1H), 7.21(d, J=8.8Hz, 1H), 7.71(d, J=15.8 Hz, 1H).

Compound 1e:

Rf: 0.75 (ethyl acetate/acetic acid/water; 30:1:1)

$^1$H NMR(CD$_3$OD) δppm: 0.86(s, 3H), 0.89(s, 3H), 0.95(s, 3H), 1.03(s, 3H), 1.06(s, 6H), 1.0–2.6(m, 24H), 2.6–2.8(m, 2H), 2.8–3.0(m, 1H), 4.15(ABq, Apart, J=12.9 Hz, 1H), 4.50(ABq, Bpart, J=12.9 Hz, 1H) , 5.63(br s, 1H), 6.33(d, J=15.8 1H) 6.85(dd, J=2.6 Hz, J=8.8Hz, 1H), 7.07(d, J=2.6 Hz, 1H), 7.12(d, J=8.8 Hz, 1H), 7.72(d, J=15.8 Hz, 1H).

Compound 1g:

Rf: 0.4 (ethyl acetate/acetic acid/water; 15:1:1)

$^1$H NMR(CDCl$_3$) δppm: 0.85(s, 6H), 0.93(s, 3H), 1.02(s, 6H), 1.06(s, 3H), 1.1–2.1(m, 20H), 2.8–3.1(m, 1H), 4.0–4.4(m, 2H), 5.60(br s, 1H), 6.38(d, 1H, J=16.0 Hz), 6.8–7.0(m, 1H), 7.11(br s, 1H), 7.4–7.5(m, 1H), 7.79(d, 1H, J=16.0 Hz).

Compound 1h:

Rf: 0.57 (ethyl acetate/acetic acid/water; 30:1:1)

$^1$H NMR(CD$_3$OD) δppm: 0.86(s, 3H), 0.89(s, 3H), 0.90(s, 3H), 0.96(s, 3H), 1.03(s, 3H), 1.06(s, 3H), 1.0–2.1(m, 20H), 2.2–2.6(m, 2H), 2.9–3.1(m, 1H), 3.40(s, 2H), 4.14(ABq, Apart, J=12.0 Hz, 1H), 4.50(ABq, Bpart, J=12.0 Hz, 1H), 5.63(br, s, 1H), 6.34(d, J=16.0 Hz, 1H), 6.86(dd, J=2.6 Hz, J=8.8 Hz, 1H), 7.08(d, J=2.6 Hz, 1H), 7.21(d, J=8.8 Hz, 1H), 7.76(d, J=10.0 Hz, 1H).

Compound 1i:

Rf: 0.18 ( chloroform/methanol; 6:1 )

$^1$H NMR(CD$_3$OD) δppm: 0.86(s, 3H), 0.91(s, 3H), 0.96(s, 3H), 1.03(s, 3H), 1.05(s, 6H), 1.0–2.1(m, 22H), 2.2–2.6(m, 6H), 2.9–3.1(m, 1H), 4.15(ABq, Apart, J=12.5 Hz, 1H) , 4.50(ABq, Bpart, J=12.5 Hz, 1H), 5.63(br s, 1H), 6.33(d, J=15.8 Hz, 1H), 6.86(dd, J=2.6 Hz, J=8.8 Hz, 1H), 7.09(d, J=2.6 Hz, 1H) 7.09(d, J=8.8 Hz, 1H), 7.70(d, J=15.8 Hz, 1H).

Compound 1k:

Rf: 0.29 (ethyl acetate/acetic acid/water; 8:1:1)

$^1$H NMR(CD$_3$OD) δppm: 0.86(s, 3H), 0.89(s, 3H), 0.95(s, 3H), 1.03(s, 3H), 1.05(s, 3H), 1.07(s, 3H), 1.0–2.1(m, 20H), 2.3–2.5(m, 2H), 2.9–3.1(m, 1H), 4.15(ABq, Apart, J=12.6 Hz, 1H), 4.46(ABq, Bpart, J=12.6 Hz, 1H), 5.68(br s, 1H), 6.28(d, J=16.0 Hz, 1H), 6.81(dd, J=2.6 Hz, J=8.8 Hz, 1H), 7.00(d, J=2.6 Hz, 1H), 7.40(d, J=8.8 Hz, 1H), 8.16(d, J=16.0 Hz, 1H).

Compound 1n:

Rf: 0.78 (ethyl acetate/acetic acid/water; 30:1:1)

$^1$H NMR(CD$_3$OD) δppm: 0.86(s, 3H), 0.89(s, 3H), 0.95(s, 3H), 1.03(s, 3H), 1.05(s, 3H), 1.06(s, 3H), 1.0–2.1(m, 20H), 2.2–2.6(m, 2H), 2.9–3.1(m, 1H), 3.80(s, 2H), 4.15(ABq, Apart, J=13.1 Hz, 1H), 4.49(ABq, Bpart, J=13.1 Hz, 1H), 5.67(br s, 1H), 6.26(d, J=15.8 Hz, 1H), 6.56(d, J=8.7 Hz, 1H), 6.78(dd, J=2.7 Hz, J=8.7 Hz, 1H), 6.88(d, J=2.7 Hz, 1H), 7.89(d, J=15.8 Hz, 1H).

The endothelin receptor antagonistic effect of compounds (I) of the present invention was evaluated using the method described in the following experimental examples. As a control, compound (50–235) which has been disclosed in WO/92/12991 (Example 1) was used.

Experiment 1

Inhibitory Effect on the Binding of $^{125}$I-Endothelin-1 to its Receptor

Smooth muscle A7r5 cells derived from rat aorta were incubated with 25 pM $^{125}$I-endothelin-1 at 37° C. for 1 hr in the presence or absence of a compound (I) of the present invention. After completion of the reaction, $^{125}$I-endothelin-1 bound to membrane fraction was separated by filtrating through glass fiber filters and the radioactivity was determined with a gamma-counter. The specific binding was calculated by subtracting the nonspecific binding which was determined in the presence of 10$^{-7}$ M non-radioactive endothelin-1 from the total binding. The concentration (nM) of the compound (I) required to achieve 50% inhibition of the specific binding (i.e., IC$_{50}$) of endothelin-1 to its receptor is shown in Table 1 below.

Experiment 2

Inhibition of the Endothelin-1-induced Increase in Cytosolic Calcium Ion Concentration To a cuvette was put a suspension of rat aortic smooth muscle A7r5 cells (Dainippon Pharmaceutical Co., Ltd.) on which 2 μM fura-2 (Dojin) has been loaded. The change in fluorescence intensity was determined with a calcium analyzer (CAF100, Nippon Bunkou Co.). In the determination, the excitation was performed at 340 nm and 380 nm and the recording at 510 nm. The cytosolic calcium concentration was calculated according to the method of Grynkiewicz et al., J. Biol. Chem., 260., pp. 3440–3450, 1985.

The experiment was carried out by adding a compound (I) of the present invention to the cell suspension in cuvette, incubating for 1 min, adding 10$^{-8}$M endothelin-1, and measuring the change in fluorescence intensity. The concentration (nM) of the compound (I) required to achieve 50% inhibition of endothelin-1-induced increase in cytosolic calcium concentration (i.e., IC$_{50}$) is shown in Table 1 below.

TABLE 1

| Compound | Activity data IC$_{50}$ (nM) | | R$^2$ |
|---|---|---|---|
| | (Ca$^{2+}$) | binding | |
| 1a | 4.5 | 24 | H |
| 1b | 2.6 | 0.5 | COCH=CHCOOH(trans) |
| 1c | 2.6 | 0.7 | COCH=CHCOONa(t) a) |
| 1d | 3.0 | 3.4 | COCH=CHCOOH(Cis) |
| 1n | 3.0 | 3.0 | CH$_2$COOH |
| 1g | 2.5 | 1.8 | COCOOH |
| 1h | 5.6 | 9.0 | COCH$_2$COOH |
| 1e | 3.5 | 3.6 | CO(CH$_2$)$_2$COOH |
| 1i | 4.6 | 6.6 | CO(CH$_2$)$_3$COOH |
| 1m | 2.7 | 5.0 | COCH=CHCOOMe(t) |
| 1k | 2.8 | 2.9 | SO$_3$H |
| 50–235 b) | 10 | 76 | | a: R$^1$ = Na

TABLE 1-continued

| | Activity data IC$_{50}$ (nM) | | |
|---|---|---|---|
| Compound | (Ca$^{2+}$) | binding | R$^2$ | b:

Experiment 3

Inhibition of Endothelin-1-induced Contradiction in Isolated Rat Thoracic Aorta

Transverse Stip specimens isolated from rat thoracic aorta were suspended in modified Locke-Ringer solution at 37° C. while aerating with mixed gas (95% O$_2$+5% CO$_2$), and the isometric tension was recorded. Four specimens derived from each rat were used in the test. Thus, three specimens were treated with compound 1c (disodium salt; prepared in Example 1 or 3) of different concentration (10$^{-8}$M, 3×10$^-$ 8M, and 10$^{-7}$M) for 10 min and the rest was untreated before the measurement of isometric tension. After the measurement, the endothelin-1 concentration-contraction curve was depicted, which proved that compound 1c shifts the concentration-contradiction curve to right in a concentration-dependent manner with pA$_2$ value of 8.8.

Experiment 4

Inhibition of Endothelin-1-induced Hypertension in Pithed Rat

Under ether anesthesia, a stainless-steal rod (diameter: 2 mm) was inserted from right orbital to spinal end of a rat. The resultant pithed rat was placed under artificial respiration and the change in blood pressure was recorded. Drugs (endothelin-1 and compound 1c prepared in Example 1 or 3) were administered intravenously. The compound 1c decreased the blood pressure in a dose-dependent manner at a dose between 0.01 and 1 mg/kg.

As shown above, the compounds (I) of the present invention can compete with endothelin for its receptors and thereby inhibiting specifically the biological activity of endothelin. Accordingly, the compounds (I) of the present invention are useful in the prophylaxis and treatment of diseases caused by excessive secretion of endothelin such as hypertension, coronary ischemia, encephalopathy, nephropathy, circulation failure of various organs, and asthma.

We claim:

1. A compound of the formula (I)

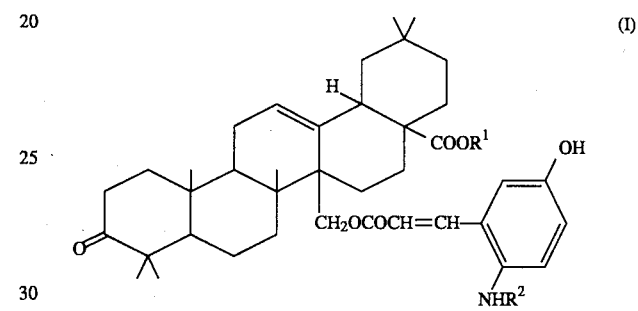

wherein R$^1$ is hydrogen or metabolic ester residue; and R$^2$ is hydrogen or —R$^3$—R$^4$ wherein R$^3$ is —SO$_3$—, —CH$_2$COO—, —COCOO—, or —COR$^5$COO— (R$^5$ is lower alkylene or lower alkenylene), and R$^4$ is hydrogen, lower alkyl or a pharmaceutically acceptable salt thereof.

2. The compound as claimed in claim 1, wherein R$^1$ is hydrogen.

3. The compound as claimed in claim 1, wherein R$^1$ is hydrogen and R$^2$ is —COCH=CHCO$_2$H.

4. A pharmaceutical composition, which comprises, as an active ingredient, the compound (I) as claimed in claim 1 together with pharmaceutically acceptable carriers therefor.

5. The pharmaceutical composition as claimed in claim 4, wherein R$^1$ is hydrogen.

6. The pharmaceutical composition as claimed in claim 5, wherein R$^1$ is hydrogen and R$^2$ is —COCH=CHCO$_2$H.

* * * * *